United States Patent [19]

Gent et al.

[11] Patent Number: 5,267,789
[45] Date of Patent: Dec. 7, 1993

[54] ECCENTRIC MOUNTED ROTOR FOR MIXING SOLIDS AND LIQUID IN A CHAMBER

[75] Inventors: Alan N. Gent, Cuyahoga Falls; Richard L. Henry, Akron, both of Ohio

[73] Assignee: University of Akron, Akron, Ohio

[21] Appl. No.: 794,384

[22] Filed: Dec. 13, 1991

Related U.S. Application Data

[63] Continuation of Ser. No. 490,838, Mar. 8, 1990, abandoned.

[51] Int. Cl.$^5$ .............................. B01F 7/16; B29B 7/10
[52] U.S. Cl. ..................................... 366/98; 366/205; 366/247; 366/285; 366/314
[58] Field of Search ........................ 366/64–66, 366/69, 96–99, 100, 205, 240–241, 261, 247, 276–279, 285, 287–288, 314, 331; 425/190, 200

[56] References Cited

U.S. PATENT DOCUMENTS

| | | | |
|---|---|---|---|
| 1,098,622 | 6/1914 | Graham | 366/241 |
| 1,279,515 | 9/1918 | Coleman | 366/285 |
| 3,155,056 | 11/1964 | Smith et al. | 366/97 X |
| 3,386,809 | 6/1968 | Massoubre | 23/285 |
| 3,612,493 | 10/1971 | Nauta | 366/287 |
| 3,963,220 | 6/1976 | Ohchi | 366/314 X |
| 4,343,929 | 8/1982 | Sugio et al. | 366/97 |
| 4,413,913 | 11/1983 | Hold et al. | 366/75 |
| 4,448,709 | 5/1984 | Bullen | 366/241 |
| 4,501,543 | 2/1985 | Rutledge et al. | 366/99 X |
| 4,552,462 | 11/1985 | Schnell | 366/287 X |
| 4,556,325 | 12/1985 | Katzin | 366/130 |
| 4,807,928 | 2/1989 | Cone | 297/151 X |
| 4,830,506 | 5/1989 | Borzenski | 366/97 X |
| 4,859,074 | 8/1989 | Asai et al. | 366/97 |
| 4,993,840 | 2/1991 | Maeda et al. | 366/314 X |

FOREIGN PATENT DOCUMENTS

| | | | |
|---|---|---|---|
| 56-45751 | 4/1981 | Japan | 366/97 |
| 0135214 | 7/1985 | Japan | 366/66 |
| 368614 | 4/1963 | Switzerland | 366/96 |

OTHER PUBLICATIONS

"The Mixing of Fluids" by Julio M. Ottino, Published in *Scientific American*, pp. 56–67, Jan. 1989.

*Primary Examiner*—Harvey C. Hornsby
*Assistant Examiner*—Charles Cooley
*Attorney, Agent, or Firm*—Oldham, Oldham & Wilson

[57] ABSTRACT

A device for mixing liquids, solids or combinations thereof, particularly viscous liquids and polymeric solids comprises a mixing vessel having therein a substantially cylindrical mixing chamber; a rotor with a cross-section in the shape of a convex-convex lens having outer convex surfaces substantially identical in shape to the inner wall surface of the cylindrical mixing chamber and with a longitudinal dimension substantially identical to that of said cylindrical mixing chamber, the rotor being variably positionable so it's rotating axis is parallel to the axis of the mixing chamber, but eccentric thereto, and mounted within the mixing chamber upon a base having a drive mechanism for the rotor disposed through it; and a lid for tightly sealing the chamber formed by the mixing vessel and the base. The rotor preferably fills from 28 to 100% of the volume of the mixing chamber; most preferably 50 to 75%. The rotor may be heliciform along its longitudinal axis.

7 Claims, 3 Drawing Sheets

ECCENTRIC MOUNTED ROTOR FOR MIXING SOLIDS AND LIQUID IN A CHAMBER

This is a continuation of copending application(s) Ser. No. 07/490,838 filed on Mar. 8, 1990 now abandoned.

This invention relates to a novel apparatus for mixing of liquids, solids, particularly powdered solids, or combinations thereof. Particular applications are found in the mixing of powders, such as the activators, promoters, accelerators, and the like, all of which are commonly known and used in the rubber industry with dough-like compositions also commonly encountered there. Even more particularly, this invention relates to a mixer that presents advantages in ease of cleaning, lack of stagnant volume, ease of replacement of internal moving parts therein, and ease of manufacture of internal moving parts, among others.

BACKGROUND OF THE INVENTION

Many practitioners in the chemical and polymer arts are limited by problems associated with achieving thorough and uniform mixtures of liquids, solids, or combinations thereof. The chemical engineering literature, for example, is replete with references as to how to achieve such mixing. It is well known that mixing, especially of high viscosity fluids, is effected by the general processes of shearing and kneading the fluid by the application of shearing forces. Processing fluids of high viscosity requires application of high torque to the mixing element in the fluid. One particular method of achieving the desired mixing is to force the fluid through a narrow gap or plurality of narrow gaps to effect the shearing and kneading.

SUMMARY OF THE INVENTION

A first aspect of this invention is to provide an easily-cleaned device for mixing high viscosity liquids, solids, particularly powdered solids, or mixtures thereof.

A second aspect of this invention is to provide a mixing device that minimizes stagnant volumes within the mixing chamber.

Another aspect of this invention is to provide a mixing device that has easily replaceable internal moving parts.

A still further aspect of this invention is to provide a mixing device that has internal moving parts that are easily manufactured.

Another aspect of the present invention is to provide a mixing device that can be fully disassembled to expedite cleaning.

The foregoing and other aspects of the invention are achieved in a device for mixing liquids, solids or combinations thereof, particularly viscous liquids and polymeric solids, comprising: a base, said base having a hole therein with a drive means disposed therethrough; a lid; a mixing vessel with first and second ends and having therein a substantially cylindrical mixing chamber, said mixing vessel being adapted at said first end with means for tight engagement with said lid and being adapted at said second end with means for tight engagement with said base such that said vessel may be variably positioned and engaged at a desired location along the length of said base; and a rotor with a cross-section in the shape of a convex-convex lens with outer radii substantially identical to the inner radius of said cylindrical mixing chamber and with longitudinal dimension substantially identical to that of said cylindrical mixing chamber, said rotor adapted on one end for engagement with said drive means.

BRIEF DESCRIPTION OF THE DRAWINGS

In the drawings, as will be more fully explained below.

ABSTRACT OF THE DRAWINGS

Figure 1:
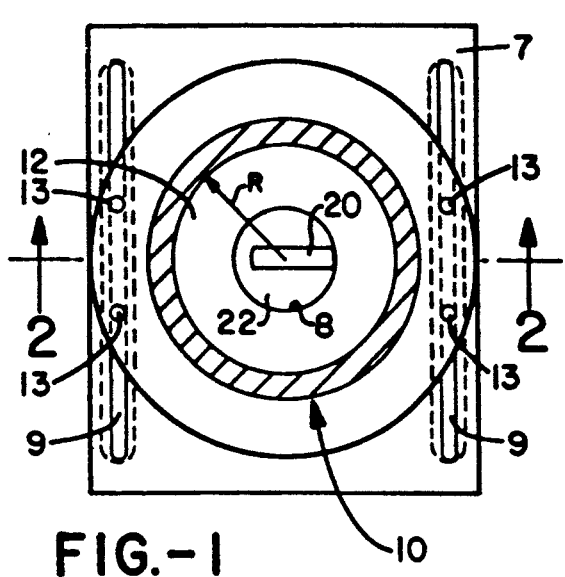
FIG. 1 is a top view of the cylindrical mixing chamber used to achieve the objectives of the present invention.

In the drawings presented herewith, the following parts are indicated by the following numbers, with corresponding parts identified by identical 7 is the base of the novel mixing device;

8 is a hole in the base of the novel mixing device;

9 are a pair of channels for engaging the base to the mixing vessel of the mixing device;

10 is the mixing vessel of the novel mixing device;

11 is a flanged portion on the mixing vessel for attaching the mixing vessel to the base;

12 is the cylindrical mixing chamber of the novel mixing device;

13 are holes in the flanged portion for engaging the base;

14 is the lid of the novel mixing device;

22 is the circular drive wheel of the novel mixing device;

18 is an engaging channel in the lower surface of the rotor;

20 is the drive tang of the novel mixing device;

30 is the rotor of the novel mixing device;

32 are enhanced flow channels incised along the sides of the rotor; and 52 and 54 are the mixing volumes of the mixing chamber created by action of the rotor in the mixing chamber.

Certain features of the rotor are indicated by letters in the drawings presented herewith, with corresponding parts indicated by identical letters:

$C_1$ and $C_2$ are the centers from which arcs WXY and YZW originate;

O is the center of the rotor cross-section;

W and Y are points at the cusps of the upper surface of the rotor, such that line WY represents the major axis of the cross-section; W' and Y' are points at the cusps of the lower surface of the rotor, such that line W'Y' represents the major axis of the cross-section; and X and Z are points at the midpoints of arcs WXY and YZW, respectively, such that line XZ represents the minor axis of the cross-section.

DESCRIPTION OF THE PREFERRED EMBODIMENT

FIG. 1 shows a top view of the preferred embodiment of the present invention, with the rotor removed to illustrate the internal detail thereof. The invention comprises a base 7 with a single circular hole 8 bored therethrough, the hole 8 being located near the center of the base 7. A pair of parallel channels 9 are formed in the base 7 on either side of the hole 8 and properly sized and adapted so as to be able to accommodate and secure the head of a bolt or other similar fastener (not shown) inside the lower portion of each channel 9, which will be better illustrated and described in a later drawing.

The mixing vessel 10 for the present invention is shown in the illustration as a hollow tube, open on both ends and having a flanged portion 11 at one end thereof. The flanged portion 11 has a plurality of holes 13 disposed therethrough, said holes 13 being parallel to the longitudinal axis of the mixing vessel 10. When the holes 13 are aligned over the channels 9 as shown in FIG. 1, a conventional fastener pair, such as a nut and bolt, may be used to secure the mixing vessel 10 to the base 7. In order to provide a tight seal, a sealing means such as a gasket may also be disposed between the base 7 and the mixing vessel 10. The preferred method of affixing the mixing vessel 10 to the base 7 requires the use of at least three fastening points, although FIG. 1 indicates four such fastening points, those being the holes 13.

It will be obvious that although FIG. 1 illustrates the mixing vessel 10 positioned atop the base 7 so that the center point of the hole 8 and the longitudinal axis of the mixing vessel 10 are coincident, the combination of the channels 9 with the holes 13 in the flange 11 allows the mixing vessel 10 to be positioned atop the base 7 at an large number of positions in relation to the hole 8 in the base 7, so that the hole 8 may easily be located eccentric to the mixing vessel 10. This capability is very important in the use of rotors of different cross-sectional areas, as will be explained later. Also, the use of a conventional drive mechanism, such as a screw drive, may be utilized to move the fasteners along the channels 9, so that the eccentricity of the hole 8 in the mixing vessel 10 may be varied to any desired extent during the mixer's operation. For example, the initial torque requirement on the rotor may be large, but decrease upon some mixing, in which case, the hole 8 would be initially positioned near the center and made more eccentric as mixing continued. Clearly the opposite situation may also be encountered with some materials.

The open volume inside the mixing vessel 10 is the cylindrical mixing chamber 12 of the invention. Although the mixing vessel 10 is shown in FIG. 1 as being a hollow tube open on both ends, it is only one representation of the vessel 10, which can be constructed in a variety of shapes and from a variety of materials, as best known to one skilled in the art.

The selected material of construction should have sufficient structural strength to endure the pressures and stresses imposed upon it by the action of the rotor upon the material to be mixed therein. The internal surfaces of the mixing vessel 12 are preferably smooth and hardened, to provide a surface that is easily cleaned after use and resists the erosion of the potentially abrasive materials used therein.

It would be obvious to one of skill in the art to incorporate a heat transfer means or similar feature to the mixing vessel 12 to allow for the addition or removal of heat or to control chamber temperature, although this feature is not critical to the operation of the invention, and is, therefore, not shown on the drawings.

The critical feature disclosed in FIG. 1 is that the cylindrical mixing chamber is circular in cross-section, which is vital to proper operation of the rotor therewithin. The cylindrical mixing chamber 12 has an internal radius R.

Focus is now directed to the area of the hole 8 bored in the base 7. The hole 8 is not empty, but rather has a circular drive wheel 22 of larger radius located below it, with a rectangular drive tang 20 affixed thereto and protruding through the hole 8 and into the cylindrical mixing chamber 12. This rectangular drive tang 20 is affixed to the upper surface of the drive wheel 22 such that it extends into the mixing chamber 12 substantially parallel to the longitudinal axis of the mixing chamber 12. This structure is discussed further below.

Figure 2:
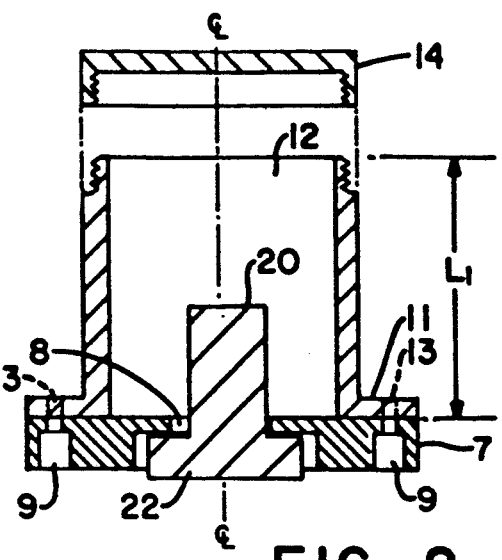
FIG. 2 is a cross-sectional side view of the cylindrical mixing chamber used to achieve the objects of the present invention.

Further features of the present invention are disclosed in FIG. 2, to which attention is now directed. This longitudinal cross-section of the invention is taken along the centerline of hole 8.

As illustrated, the cylindrical mixing chamber 12 formed by the combination of the base 7 and the mixing vessel 10 is closed on the bottom end of the vessel by the fastening of the channels 9 in the base 8 and the holes 13 in the flange portion 11 of the vessel 10 by a plurality of fastening means (not shown).

At the end of the vessel 10 opposite the flanged portion 11, the vessel 10 is threaded to accept a threaded lid 14. In this manner, the cylindrical mixing chamber 12 can be tightly sealed. Although FIG. 2 indicates threading on the external surface of the vessel 10 to accommodate internal threading on the lid 14, it will be understood that the essence of this feature is to provide a tight seal to prevent loss of the mixing chamber's contents, once it is filled. It will therefore be appreciated that other sealing means are well known and may be effectively substituted for that disclosed in the drawing. It is important to note that the overall height of the mixing chamber 12, from the base 7 to the lid 14, is dimension $L_1$, which is also a critical dimension of the rotor.

It should also be noted at this point that it is very important to the correct operation of the rotor within the chamber 12 that the rotor must fit tightly between the lid and the base so that flow of the material being mixed is between the cusps of the rotor and the chamber wall and not over or under the rotor. For this reason, it may be necessary to "shim" the upper and lower surfaces of the rotor with a sacrificial sealing surface.

The critical features of the present invention presented in this Figure are that the mixing chamber 12 is a right circular cylinder of internal radius R and length $L_1$.

FIG. 2 also shows some detail of the drive wheel 22 and drive tang 20. The drive tang 20 is firmly attached, to, or, preferably, integral to, the drive wheel 22. The drive tang 20 is positioned radially on the drive wheel 22, and it is eccentrically positioned with relation to the center of the drive wheel 22. The drive wheel 22 is attached to a drive mechanism (not shown) on the side opposite the drive tang 20, which drive mechanism can urge the drive wheel 22 against the base 7 and cause the drive wheel 22 to rotate about the center line of the hole 8. The exact method of retaining the drive wheel 22 in juxtaposition to the hole 8 and providing a seal while the drive wheel 22 rotates about the hole 8 are matters that are well within the skill of persons in this art, and several alternatives will be immediately known to such persons.

The drive tang 20 should extend into the mixing chamber 12 a sufficient distance to firmly engage the rotor when the rotor is positioned atop it, as further discussed below. Typically, this will mean that the drive tang 20 should be at least 0.1 $L_1$ in height, and, in most cases, it will be less than 0.5 $L_1$.

Figure 3:
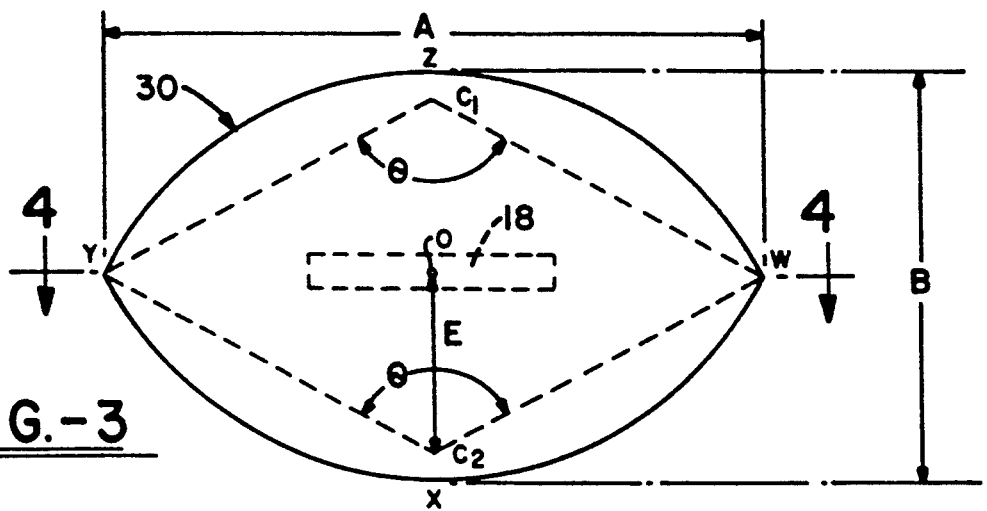
FIG. 3 is a top view of one embodiment of the novel rotor, showing its cross-section.

FIG. 3 is a top view of the rotor 30 that is placed inside the cylindrical mixing chamber 12. The rotor 30 has a cross-section that resembles a convex-convex lens, that is, it has a major axis indicated by line WY of length A and a minor axis indicated by line XZ of length B, about each of which the rotor 30 is symmetrical. The center of the rotor cross-section is located at the point where lines WY and XZ intersect, that is, point O on FIG. 3.

In a first embodiment of the rotor 30, corresponding points on the top and bottom surfaces of the rotor are aligned with each other when viewed along the longitudinal axis of the rotor 30, that is, the rotor 30 is a right solid and is not heliciform. Other contemplated embodiments of the rotor 30 are presented separately later in this disclosure, Another way of viewing the rotor 30 is to consider it as the symmetrical solid formed when two right cylindrical segments of identical radius R and chord length A are joined along that chord length. For example, viewing the cross-section in FIG. 3, the rotor 30 is comprised of the circular segment WXY and the circular segment YZW, the former of which is a segment of a circle centered at C1 and subtending an angle $\theta$ and the latter of which is a segment of a circle centered at C2 and subtending an identical angle $\theta$.

The offset distance of the points C1 and C2 from the center 0 of the rotor is determinable by well-known geometry and is indicated in FIG. 3 as E. The radius of each of the segments is equal to R, the radius of the cylindrical mixing chamber 12. The chord length, which would be indicated on FIG. 3 as the length A of the major axis or the distance between Y and W, can be shown geometrically to be smaller than twice the radius R of the mixing chamber 12, because the cross-sectional area of the rotor 30 is necessarily smaller than that of the mixing chamber 12. More specifically, length A of the major axis can be shown to be $2(R^2-E^2)$. Likewise, the length B of the minor axis, which is equal to the distance from X to Z, can be shown to be $2(R-E)$.

The preferred range of cross-sectional area to be filled by the rotor 30 is from about 50% to about 75%. Because of features discussed below involving the rotation of the rotor 30, the practical lower limit of cross-sectional area to be filled is about 28%. The upper limit of cross-sectional area to be filled is somewhat less than 100%, as is obvious by the need to be able to rotate the rotor 30 in the chamber 12 and the economics of increasing rotor cross-section and decreasing mixing volume. Clearly, it will be understood that since the open volume of the mixer is proportional to the cross-section, any rotor that fills a given area when viewed in cross-section will fill an identical portion of the mixer volume when viewed overall.

A rotor 30 of the present invention can be manufactured once the dimensions therefor are set by determining the desired percentage of chamber cross-sectional area to be filled. For example, a rotor 30 is desired which will fill about 70% of the chamber cross-sectional area. By conventional geometry, the total area of the chamber with radius R is 3.14159 $R^2$, so 70% would be 2.200 $R^2$. Recall that the rotor consists of two identical segments, so each segment must have area of 1.100 $R^2$. By geometrical calculations that are well known or from tables that are commonly published, such as Table 1-5a on page 1-22 of the Chemical Engineer's Handbook (5th edition, 1973) by Perry and Chilton, it is determined that the central angle $\theta$ of each segment is about 153°, that the length A of the major axis or distance YW is about 1.945 R, and that the length B of the minor axis or distance XZ is about 1.533 R. Since the offset distance E is the difference between the radius R and one-half of the length of the minor axis, the offset distance E is about 0.234 R.

Similarly, a rotor 30 to fill 60% of the cross-sectional area of a chamber with radius R is found to have a central angle $\theta$ of between 142 and 143°, a major axis length A of about 1.892 R, a minor axis length B of about 1.356 R, and an offset distance E of about 0.322 R.

One method of manufacturing the first embodiment disclosed herein of rotor 30 is to cut the rotor from a piece of bar or rod stock on a conventional lathe. By setting the workpiece up in the lathe such that the workpiece rotates not about the center point O, but instead rotates about point C1, the arc segment WXY can be cut at a distance R from point C1. After resetting the workpiece in the lathe such that the piece rotates about point C2, the arc segment WZY can be cut at a distance R from point C2. Once the cross-section is prepared, the length of the rotor can be adjusted by making a cut parallel to the cross-section.

Figure 4:
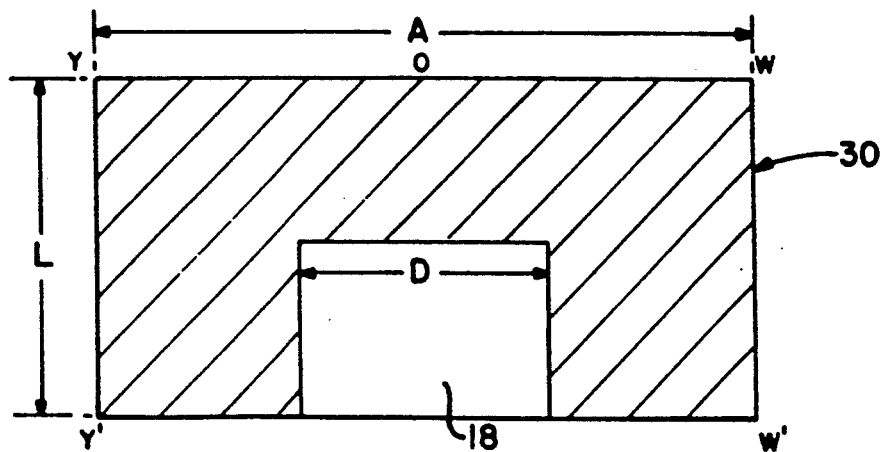
FIG. 4 is a side view of the rotor of FIG. 3, taken along the center line 4—4 of the rotor shown in FIG. 3.

FIG. 4 is a sectional view of the rotor 30, taken along Line 4—4 in FIG. 3. As is indicated in the FIG. 4, a rectangular channel 18 is routed into the lower surface of the rotor 30 to engage the drive tang 20 which is positioned in the lower portion of the mixing chamber 12 as described above. The drive tang 20 is positioned such that its center is located less than a distance E from the center of the bottom of the mixing chamber 12, which distance E is determined by the offset of the specific rotor selected, as described above. This offset or eccentricity of the drive tang 20 can be altered by moving the mixing vessel 10 with relation to the base, as described above. The drive tang 20 should extend into the mixing chamber 12 to a length sufficient to effectively engage the inner surfaces of the channel 18, again, as described above.

The channel 18 is centered under point O and proportioned such that, when it engages the drive tang 20, the drive tang 20 is able to move reciprocally in the channel 18 along the direction of the rotor's 30 major axis, but the drive tang 20 is essentially constrained from motion in the direction of the rotor's 30 minor axis. The channel 18 has a length D along the major axis of the rotor 30 such that at least one end of the rotor 30 can approach the wall of the chamber 12 arbitrarily close at any point in the sweep of the rotor 30 in the chamber 12, and, thus, the entire chamber 12 is swept by the rotor 30 every rotation, eliminating any stagnant points in the chamber and assuring good mixing. The exact mechanism of this rotation is described more fully below.

Well-known geometric principles will show that this sweeping of the chamber's 12 inner wall can occur when the channel 18 has a length D such that the drive tang 20 can slide within the channel 18 to a position located a distance R+E from the opposite end of the major axis.

It can be shown, from the commonly available tables referenced above, that when a rotor 30 is designed to fill about 28% of the chamber area or less, the offset E is sufficiently large and the dimension A is sufficiently small that the drive tang 20 cannot be constrained within the rotor 30 and simultaneously permit the rotor 30 to be able to approach arbitrarily close to the entire inner wall surface of the chamber 12. For this reason, the lower limit of rotor cross-sectional area permitted by this invention is effectively about 28%.

Figure 5:
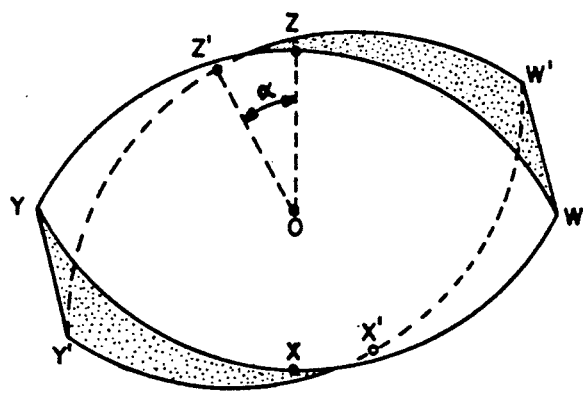
FIG. 5 is a top view of a second embodiment of the rotor.

A second method of designing a rotor 30 of the present invention is disclosed in FIG. 5. Although the rotor 30 disclosed here is identical to the rotor 30 of FIG. 3 at any given cross-section, a "twist" has been uniformly imposed along the longitudinal axis of the rotor 30, so that a heliciform solid is achieved. In the specific example shown in FIG. 5, a total "twist" of $\alpha$ degrees has been imposed from the top (surface WXYZ) to the bottom (surface W'X'Y'Z') of the rotor 30.

The purpose of introducing helical twist to the rotor 30 is to promote or induce axial flow of the materials being mixed. It is a well-known principle that good mixing of materials in a cylindrical vessel requires such axial flow in addition to the circumferential and radial flows that are induced by the rotor.

Figure 6:
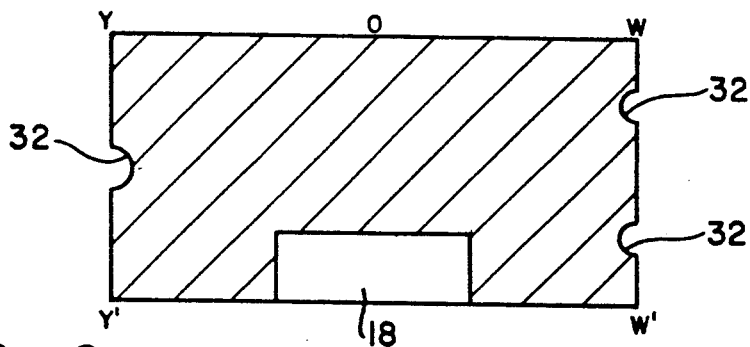
FIG. 6 is a side view of a third embodiment of the rotor.

An alternate or additional method of inducing axial flow in the rotor 30 of the present invention is disclosed in FIG. 6. Here, the rotor 30 of FIGS. 3 and 4 has had a plurality of enhanced flow channels 32 incised along lines YY' and WW' of the rotor's height. The specific flow channels depicted are smoothly rounded, but alternate shapes may be found to be effective. The total amount of new flow area opened up by the flow channels 32 should be approximately the same at each cusp end of the rotor 30, but the longitudinal placement of the opposing flow channels 32 should be varied so as to enhance the axial flow of material. In the specific case illustrated, for example, the two flow channels 32 on the line WW' should each have about one-half the area of the single flow channel 32 on the line YY'.

Figures 7A, 7B:
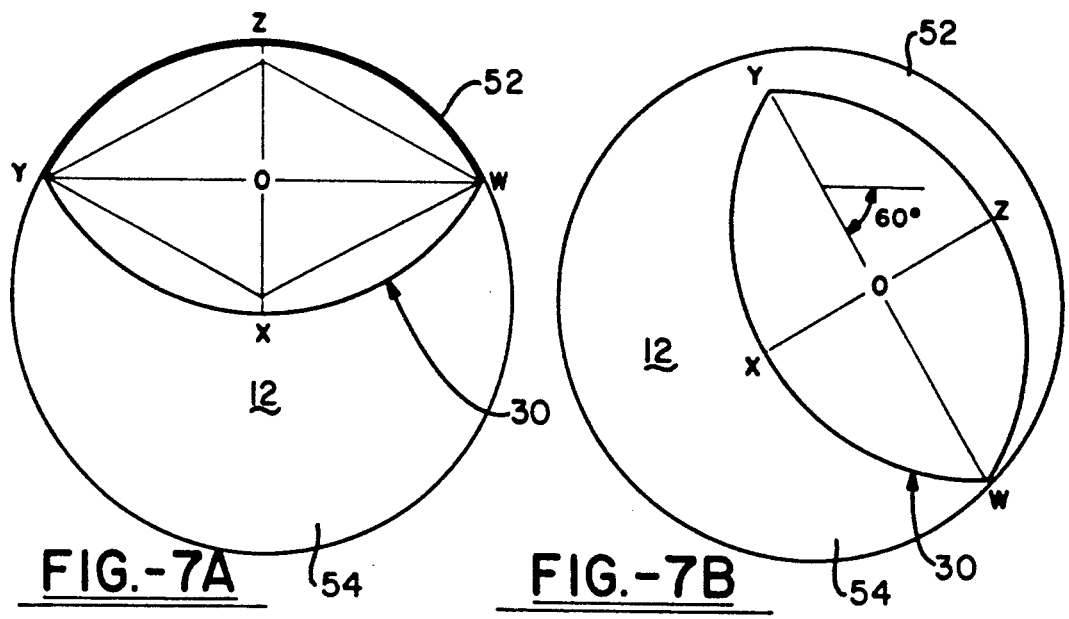
FIG. 7A through 7D show the mechanism of rotation of the rotor within the mixing chamber, as viewed from the top of the mixing chamber.

Referring now to FIGS. 7A through 7D, the sweeping mechanism of the rotor 30 in the mixing chamber 12 is illustrated. In FIG. 7A, the rotor 30 is initially placed into the mixing chamber 12 such that the drive tang 20 is centered beneath the center O of the rotor 30. When this occurs, one entire circular segment WZY or WXY can be positioned arbitrarily close to the inner wall of the mixing chamber 12, effectively dividing the open area of the chamber 12 into two areas, designated as 52 and 54, respectively, the first of which, 52, is defined as the area between rotor segment WZY and the vessel walls and the second of which, 54, is defined as the area between rotor segment WYX and the vessel walls. In this initial state, he first area 52 has essentially no area, as WZY is arbitrarily close to the vessel walls. Correspondingly, area 54 contains all of the open area with the mixing chamber 12.

As the drive tang 20 rotates 60° clock-wise and causes rotor 30 to move 60° similarly, to the position shown in FIG. 7B, the first area 52 has increased and the second area 54 has correspondingly decreased. It is, of course, very obvious that the total open area of mixing chamber is determined by the area of the rotor 30 and is simply the sum of areas 52 and 54. It may not be quite as obvious, but the direction of rotation of the rotor is not relevant to the operation of the mixer and rotation in a clock-wise fashion is only a matter of choice to illustrate the mechanism.

Figures 7C, 7D:
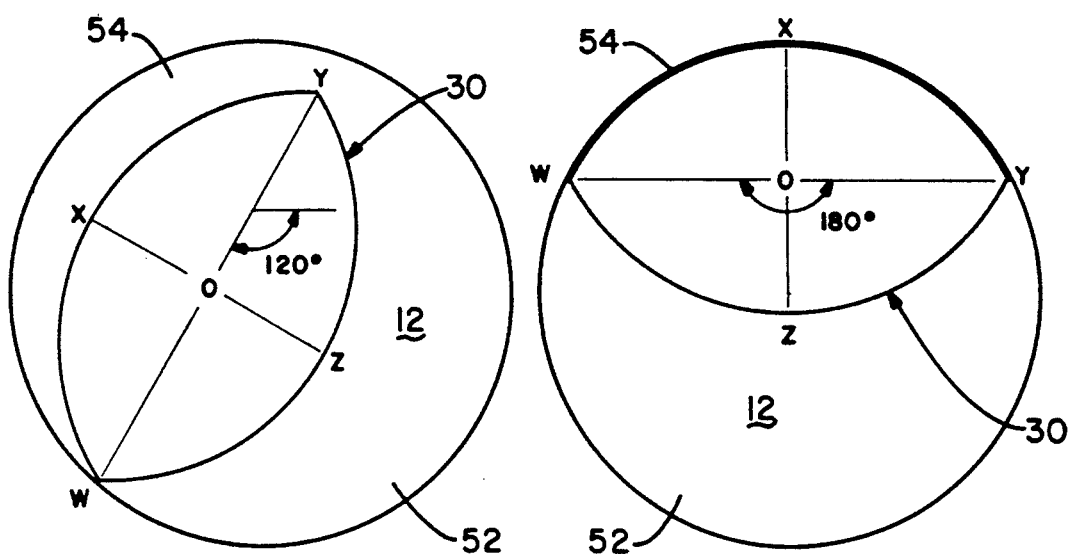

In FIG. 7C, the rotor 30 has moved to a position 120° clock-wise from the starting point and area 52 has again increased at the expense of area 54. It will be appreciated that the movement of material from area 54 to area 52 is occurring by a flow of the material through the planar area defined by the top and bottom of the mixer, the point Y of the rotor 30 and the vessel wall.

In FIG. 7D, the rotor 30 has moved 180° clock-wise from the from the starting position of FIG. 7A. All of the material initially contained within area 54 has been transferred to area 52, which now has all of the open area of the mixing vessel, as area 54 has decreased essentially to zero by becoming arbitrarily close to the wall.

Clearly, it is obvious, without further need of illustration, that the continued rotation through another 180° of clock-wise movement will be identical to the first cycle illustrated in 7A through 7D, the only difference being the transfer of material from area 52 back to area 54. In this manner, the full contents of the mixer are transferred from one side of the rotor and back again within each full rotation. The requisite passage through the flow restriction at point Y provides the shearing and kneading imposed upon the material.

From the above description of the present invention, it will be readily appreciated that the mixing device is capable of being fully disassembled into a number of separate parts with mostly smooth, non-angular surfaces that may be easily cleaned. In this manner, the objective of easy cleaning is achieved.

Also from the above description, it will be readily appreciated that the mobility of the vessel 10 on the base 7 enables the drive tang 20 to be positioned at varying distances from the center of the mixing chamber 12. In this manner, rotors 30 of various cross-sectional areas may be substituted one for another in the same mixing chamber and each such rotor may be optimally positioned, due to the mobility of the vessel 10.

While in accordance with the patent statutes a preferred embodiment and best mode have been presented, the scope of the invention is not limited thereto, but is to be measured by the scope of the attached claims.

What is claimed is:

1. A device for mixing liquids, solids or combinations thereof, particularly viscous liquids and polymeric solids, comprising:

a base, said base having a hole therein with a drive means disposed therethrough;

a lid;

a mixing vessel with first and second ends and having therein a substantially cylindrical mixing chamber having a longitudinal axis and an inner wall surface, said mixing vessel including at said first end means for tightly engaging said lid and including at said second end means for tightly engaging said base such that said vessel may be variably positioned and engaged at a desired location along the length of said base; and means to position the drive means eccentric to the axis of the mixing vessel, a rotor with a longitudinal axis and a cross-section in the shape of a convex-convex lens, said rotor having outer convex surfaces substantially identical in shape to the inner wall surface of said cylindrical mixing chamber said rotor having longitudinal dimension substantially identical to that of said cylindrical mixing chamber, said rotor including on one end means for engagement with said drive means, said drive means rotating the rotor about an eccentric axis which is parallel to the axis of the mixing chamber such that each convex surface of the rotor comes into a close spaced conformance to the inner wall surface of the mixing chamber at least once per full revolution of the rotor relative to the chamber.

2. The device of claim 1 wherein the rotor is heliciform along its longitudinal axis.

3. The device of claim 1 wherein the rotor has flow channels along said rotor's longitudinal dimension.

4. The device of claim 1 wherein said rotor is sized to occupy from about 28 percent to about 100 percent of the total volume of said mixing chamber.

5. The device of claim 4 wherein said rotor is sized to occupy from about 50 percent to about 75 percent of the total volume of said mixing chamber.

6. The device of claim 1 where the drive means is a drive tang affixed to a drive wheel, said drive wheel being external to the mixing chamber, said drive tang extending into the mixing chamber through said hole in said base.

7. The device of claim 1 wherein the means for tightly engaging said base comprises:
 a pair of parallel channels on said base along said length;
 a flanged portion at the second end of said mixing vessel, with a plurality of holes disposed through said flanged portion; and
 means for engaging said vessel to said base.

* * * * *